United States Patent
Young et al.

(10) Patent No.: US 9,847,767 B2
(45) Date of Patent: Dec. 19, 2017

(54) ELECTRONIC DEVICE CAPABLE OF ADJUSTING AN EQUALIZER ACCORDING TO PHYSIOLOGICAL CONDITION OF HEARING AND ADJUSTMENT METHOD THEREOF

(71) Applicant: Unlimiter MFA Co., Ltd., Eden Island, SC (US)

(72) Inventors: Neo Bob Chih-Yung Young, Taipei (TW); Kuo-Ping Yang, Taipei (TW)

(73) Assignee: UNLIMITER MFA CO., LTD., Eden Island (SC)

( * ) Notice: Subject to any disclaimer, the term of this patent is extended or adjusted under 35 U.S.C. 154(b) by 96 days.

(21) Appl. No.: 14/992,070

(22) Filed: Jan. 11, 2016

(65) Prior Publication Data
US 2017/0126193 A1    May 4, 2017

(30) Foreign Application Priority Data
Nov. 3, 2015   (TW) .............. 104217587 U

(51) Int. Cl.
| H03G 5/00 | (2006.01) |
| H03G 5/16 | (2006.01) |
| A61B 5/12 | (2006.01) |
| H03G 5/02 | (2006.01) |

(52) U.S. Cl.
CPC ............... *H03G 5/165* (2013.01); *A61B 5/12* (2013.01); *H03G 5/025* (2013.01)

(58) Field of Classification Search
CPC .......... H03G 5/165; H03G 5/025; A61B 5/12
USPC ......................................... 381/103
See application file for complete search history.

(56) References Cited

U.S. PATENT DOCUMENTS

2015/0281853 A1* 10/2015 Eisner ................ H04R 25/505
                                                            381/312

* cited by examiner

*Primary Examiner* — Paul S Kim
(74) *Attorney, Agent, or Firm* — Bacon & Thomas, PLLC

(57) ABSTRACT

Disclosed is an electronic device comprising an equalizer and an equalizer adjustment system. The equalizer adjustment system for adjusting the settings of the equalizer comprises a testing module, a parameter calculation module and a parameter setting module. The testing module is used to provide a hearing test procedure for assessing a user's physiological condition of hearing so that after the user completes the hearing test procedure, the parameter calculation module and the parameter setting module can adjust the settings of the equalizer according to the user's physiological condition of hearing.

18 Claims, 9 Drawing Sheets

ELECTRONIC DEVICE CAPABLE OF ADJUSTING AN EQUALIZER ACCORDING TO PHYSIOLOGICAL CONDITION OF HEARING AND ADJUSTMENT METHOD THEREOF

BACKGROUND OF THE INVENTION

1. Field of the Invention

The present invention relates to a technique for adjusting an equalizer, and particularly to a technique for adjusting an equalizer according to the user's physiological condition of hearing.

2. Description of the Related Art

An equalizer (EQ) is a tool for adjusting sound output. The equalizer can change the gain values of sounds at different frequencies to modify the relative volumes of sound in various frequency ranges. Most existing computers are equipped with equalizer software, which can be used to modify an audio signal when users listen to music so as to provide entertainment effect.

Elderly or hearing-impaired people have an impaired ability to hear higher frequency sounds. If the equalizer can be applied to adjust the high-frequency bands of sounds, it would help them to hear the sounds more clearly.

SUMMARY OF THE INVENTION

It is a major objective of the present invention to provide an electronic device and a method which can adjust equalizer settings according to the user's physiological condition of hearing.

It is another objective of the present invention to provide an audio playback device capable of changing the equalizer settings according to the user's physiological condition of hearing.

To achieve the major objective described above, an electronic device of the present invention includes an equalizer and an equalizer adjustment system, wherein the equalizer adjustment system is used to adjust the settings of the equalizer. The equalizer adjustment system includes a testing module, a parameter calculation module, and a parameter setting module. The testing module is used for providing a hearing test procedure to acquire a plurality of minimum gain values at which sounds at different frequencies can be heard by the user. The parameter calculation module is used to generate a correction processing parameter according to each of the minimum gain values and a reference gain value. The parameter setting module is used for adjusting the settings of gain values of sounds at different frequencies of the equalizer according to the correction processing parameter.

To achieve another objective described above, the audio playback device provided in the present invention can be electrically connected to an electronic device. Specifically, the audio playback device includes a second audio processing chip, a signal receiver, and an equalizer. The signal receiver is electrically connected to the second audio processing chip and is used to receive a parameter setting command from the electronic device. The parameter setting command is used for adjusting gain value settings of the equalizer with regard to sounds at different frequencies.

The method for adjusting an equalizer of the present invention is applied to an electronic device and used to adjust the settings of an equalizer. The method for adjusting an equalizer includes the following steps: providing a hearing test procedure so as to acquire a plurality of minimum gain values at which sounds at different frequencies can be heard by a user after the user finishes the hearing test procedure; generating a correction processing parameter according to each of minimum gain values and a reference gain value; and adjusting the settings of gain values of sounds at different frequencies of the equalizer according to the correction processing parameter.

DETAILED DESCRIPTION OF THE PREFERRED EMBODIMENT

Hereafter, the technical content of the present invention will be explained with reference to preferred embodiments.

Figure 1:
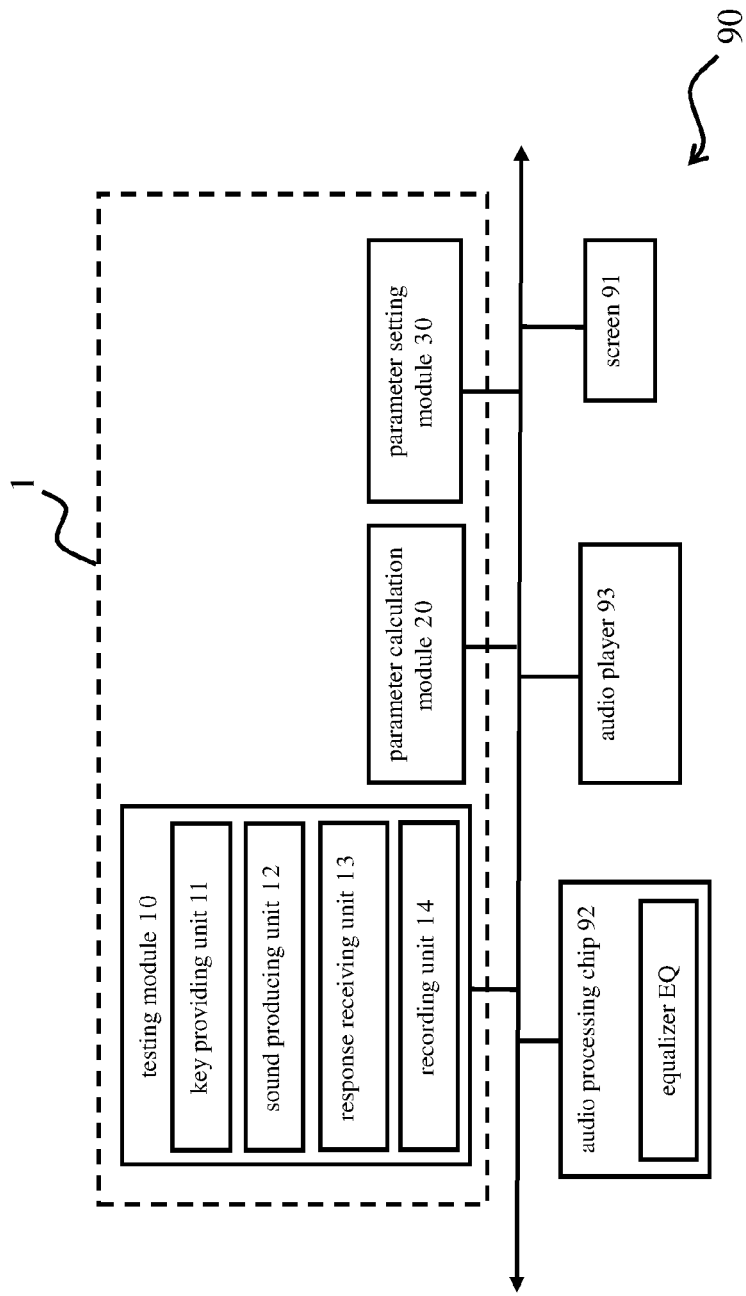
FIG. 1 presents schematically the environment of an electronic device including an equalizer adjustment system according to a first embodiment of the present invention.

Hereinafter, please refer to FIG. 1 to FIG. 8. FIG. 1 presents schematically the environment of an electronic device 90 of the present invention. As shown in FIG. 1, in the first embodiment of the present invention, the electronic device 90 of the present invention includes a screen 91, an audio processing chip 92, an audio player 93, an equalizer EQ, and an equalizer adjustment system 1. The equalizer adjustment system 1 is electrically connected to the screen 91, the audio processing chip 92 and the audio player 93. In a specific embodiment of the present invention, the electronic device 90 is a smart phone, but the present invention is not limited thereto. The electronic device 90 may also be a tablet computer, laptop or other electronic product with computing processing capability.

Figure 5:
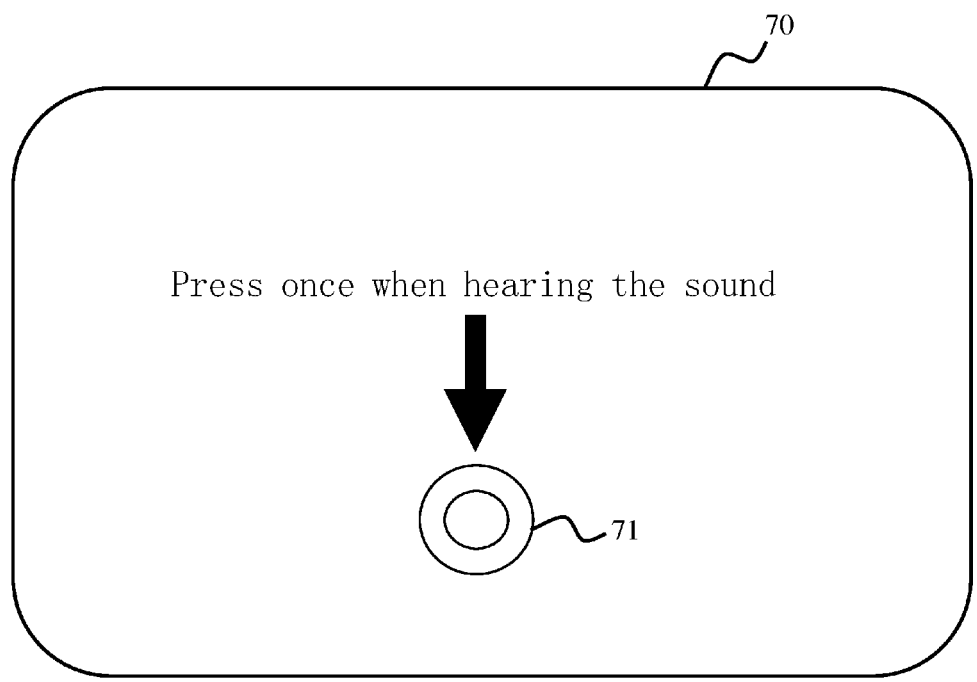
FIG. 5 is a schematic diagram of a test interface.

The screen 91 is used for displaying video images. In an embodiment of the present invention, the screen 91 can display a test interface 70 as shown in FIG. 5, such that the user can conduct a hearing test through the test interface 70 (as described later).

Figure 3:
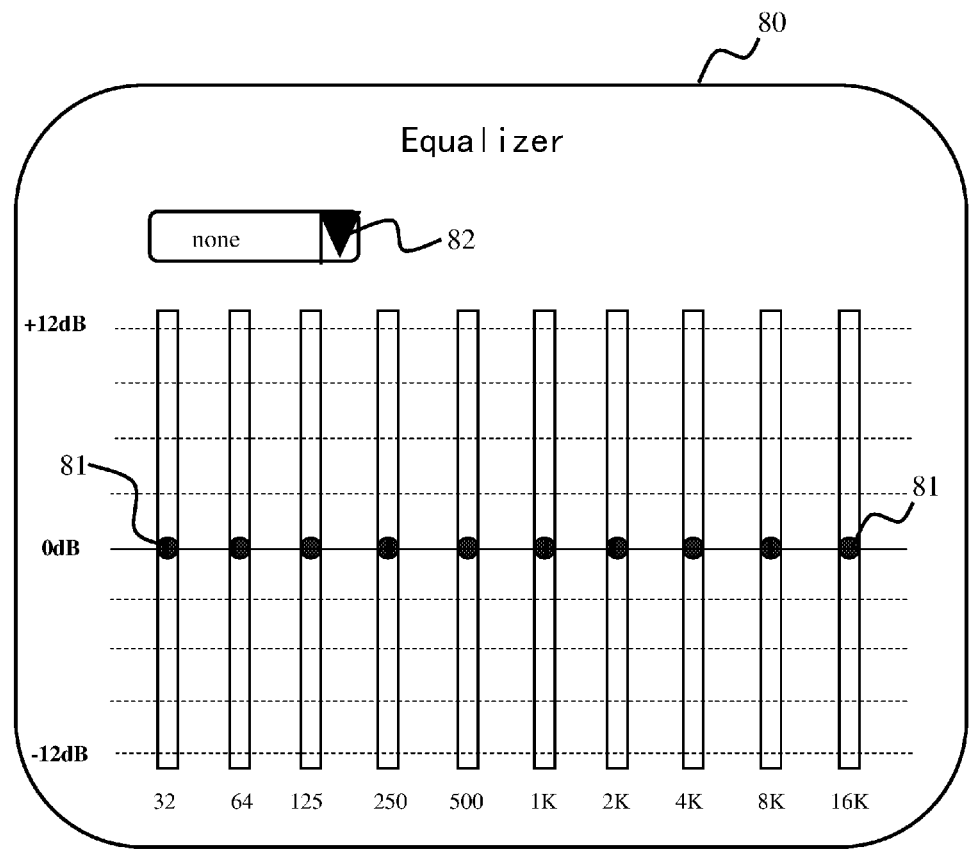
FIG. 3 is a view of the gain value settings of an equalizer in normal mode.
Figure 4:
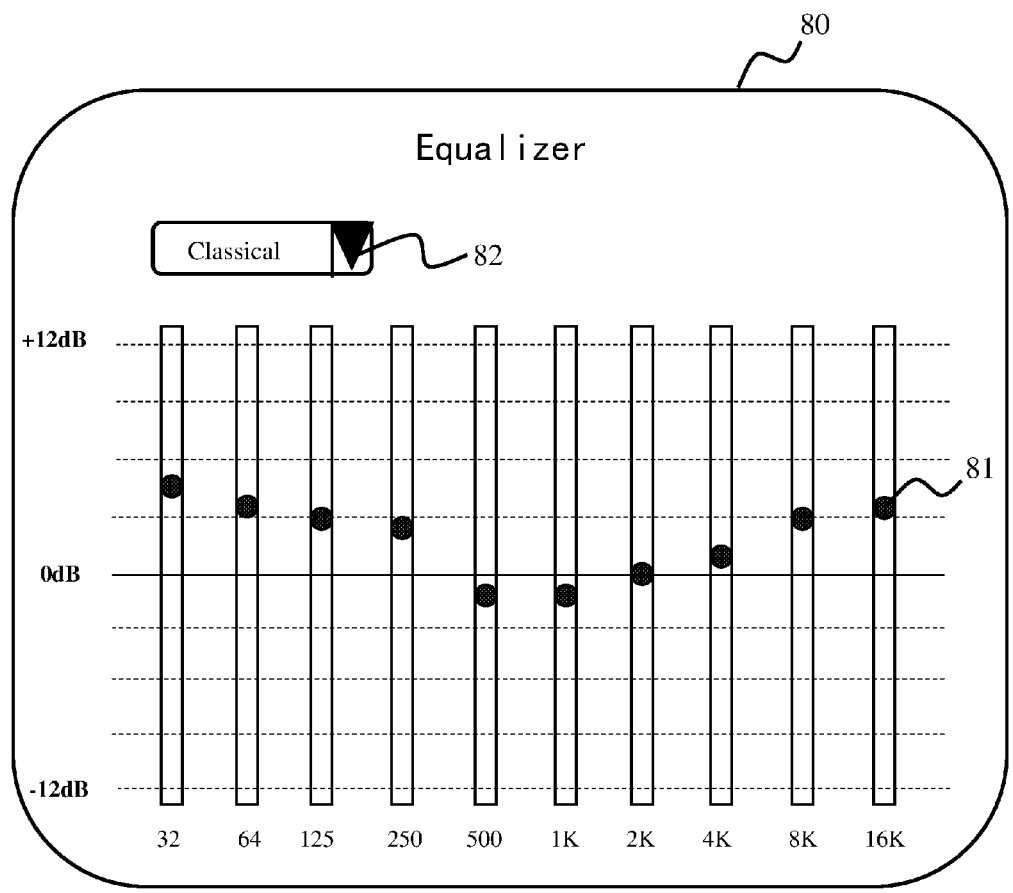
FIG. 4 is a view of the gain value settings of an equalizer in another mode.

In the first embodiment of the present invention, the audio processing chip 92 is used for performing audio encoding and decoding. The audio processing chip 92 is loaded with equalizer EQ software (firmware). In other words, in this embodiment, the equalizer EQ is disposed in the audio processing chip 92. It can adjust the gain values of sounds at different frequencies outputted by the audio processing chip 92 to adjust the settings of the gain values of the equalizer EQ. In general, the adjustment of gain values of the equalizer EQ can be performed by users through a graphical interface 80 as shown in FIGS. 3 and 4. FIG. 3 shows the settings of the gain values of the equalizer EQ in normal mode. If the equalizer EQ is in normal mode, the gain values of sounds at each frequency are equivalent. If a user would like to increase the volume of a particular frequency range of the outputted sound, the user can manually increase the gain value of an adjustment knob 81 in the high-frequency portion (2~16 kHz). In addition, the existing equalizer EQ has a plurality of preset modes available for users to select. The user can select a desired mode through a mode menu 82. FIG. 4 shows the settings of the gain values of the equalizer EQ in another mode. The settings of the gain values vary according to mode. Since the equalizer EQ is a common tool for adjusting sound output, its stricture and principles are apparent to those skilled in the art and thus will not be repeated herein.

The audio player 93 may be a built-in speaker or an external headphone, which is used for producing sounds according to sound signals generated and encoded by the audio processing chip 92.

In the first embodiment of the present invention, the equalizer adjustment system 1 includes a testing module 10, a parameter calculation module 20 and a parameter setting module 30. It should be noted that the aforementioned modules not only can be configured as hardware devices, software programs, firmware or a combination thereof, but also can be configured as a circuit loop or in other suitable ways. Also, each of the modules can be individually configured or configured in combination with others. In a preferred embodiment, each module is a software program stored in the memory, and each module is executed by a processor (not shown) in the electronic device 90 to achieve the function of the present invention. In addition, the present embodiments are only illustrative of preferred embodiments. To avoid redundancy, all of the possible combinations of changes are not described in detail herein. However, those skilled in the art should appreciate that none of the individual modules are necessary. For the implementation of the present invention, an embodiment may also contain other detailed conventional modules or elements. Each module or component is likely to be omitted or modified depending on demand. Also, other modules or elements may not necessarily exist between any two modules.

In an embodiment of the present invention, the testing module 10 includes a key providing unit 11, a sound producing unit 12, a response receiving unit 13 and a recording unit 14.

The key providing unit 11 is used to provide a test interface 70 as shown in FIG. 5 on the screen 91, wherein the test interface 70 includes a virtual key 71.

Figure 6:
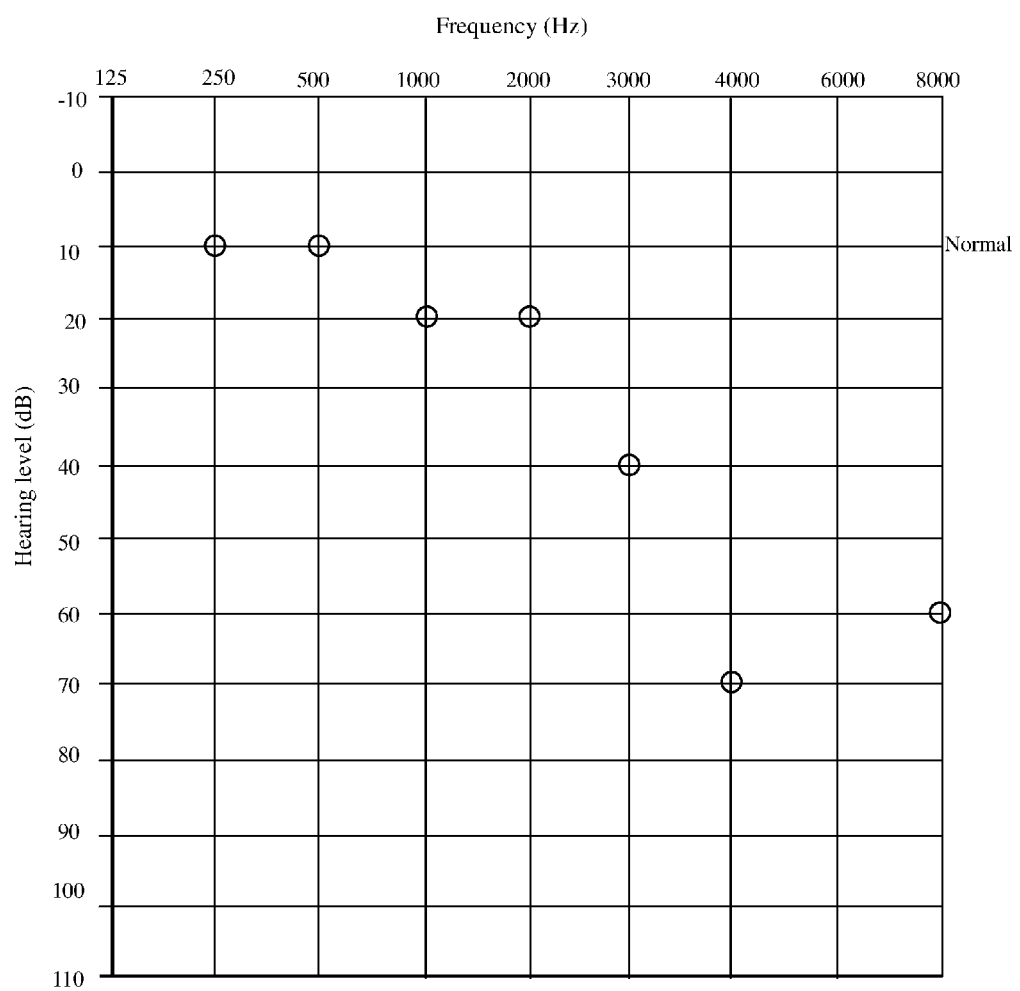
FIG. 6 is a view of a hearing test result.

The sound producing unit 12 is used for controlling the audio player 92 to make a plurality of test sounds with different frequencies. As shown in FIG. 6, in an embodiment of the present invention, the frequencies of each of the test sounds are 250 Hz, 500 Hz, 1,000 Hz, 2,000 Hz, 3,000 Hz, 4,000 Hz, and 8,000 Hz, respectively. Moreover, a test sound at a same frequency includes a plurality of sound segments with different gain values. The gain values of each of the sound segments increase in sequence by 10 dB over the previous gain value in an arithmetic sequence with a difference between any two neighboring segments of 10 dB, but the present invention is not limited thereto.

The response receiving unit 13 is used for receiving a response command inputted by clicking the virtual key 71 when the user hears each of the test sounds.

The recording unit 14 is used for acquiring minimum gain values at which sounds at different frequencies can be heard by the user according to each of the received response commands. For example, as shown in FIG. 5, if the sound producing unit 12 issues a test sound at the frequency of 250 Hz and the user can hear the test sound when the gain value is 10 dB, the user will press the virtual key 71 to input a response command. The recording unit 14 will acquire and record a minimum gain value of 10 dB as the gain value at which the user can hear a sound at a frequency of 250 Hz according to the received response command. Also, if the sound producing unit 12 issues a test sound at the frequency of 4,000 Hz, but the user does not hear the test sound or press the virtual key 71 until a gain value of 70 dB is applied, the recording unit 14 will acquire and record a minimum gain value of 70 dB as the gain value at which the user can hear a sound at a frequency of 4,000 Hz according to the received response command.

Thus, through the implementation of each of the units, the testing module 10 can provide a hearing test procedure to acquire a plurality of minimum gain values at which sounds at different frequencies can be heard by a user (as shown in FIG. 6) after the user finishes the hearing test procedure. However, it should be noted that the hearing test procedure here is not limited to the above described manner, and the implementation of the present invention can also be combined with existing hearing test methods to provide different hearing test procedures. Since using the hearing test to acquire minimum gain values at which sounds at different frequencies can be heard by users is a known technique, the related methods and principles are apparent to those skilled in the art, and many patent documents are found to have records, the related details will not be repeated herein.

The parameter calculation module 20 is used for generating a correction processing parameter according to each of the minimum gain values and a reference gain value acquired through the test. In an embodiment of the present invention, the parameter calculation module 20 uses the smallest gain value among the minimum gain values acquired by the test as the reference gain value. In FIG. 6, for example, among a plurality of minimum gain values, the smallest are 10 dB (those at 250 Hz and 500 Hz). Thus, the parameter calculation module 20 would use 10 dB as the reference gain value. In other words, in the present embodiment, the reference gain value is dynamic and can be determined based on the test results, but the determination of the reference gain value in the present invention is not limited thereto. The reference gain value can also be uniformly preset as a specific gain value (e.g., 20 dB).

In the present embodiment, the parameter calculation module 20 generates the correction parameter based on the difference between each of the minimum gain values and the reference gain value. Using 4,000 Hz as an example, if the minimum gain value is 70 dB, the parameter calculation module 20 will generate a correction parameter according to the difference of 60 dB between the minimum gain value and the reference gain value. Similarly, correction parameters at other frequencies will also be acquired in this way. Ultimately, all the correction parameters for the different frequencies are assembled as the correction processing parameter as described above.

The parameter setting module 30 is used to generate a parameter setting command according to the correction processing parameter. The parameter setting command is used for adjusting the settings of the gain values of sounds at different frequencies of the equalizer EQ. In an embodiment of the present invention, when the acquired minimum gain value of sounds at a specific frequency is greater than the reference gain value 10×N dB (0<N<20, where N is usually an integer when doing a test), the parameter setting module 30 will increase the gain values of sounds corresponding to each of the frequencies of the equalizer by N dB. For example, in the above example, if the acquired minimum gain value at which a sound at the frequency of 4,000 Hz can be heard by the user is 70 dB, whose difference with the reference gain value 10 dB is 60 dB, then at this time, the parameter setting module 30 will increase the gain value of sounds at the frequency of 4,000 Hz of the equalizer EQ by 6 dB.

Figure 7:
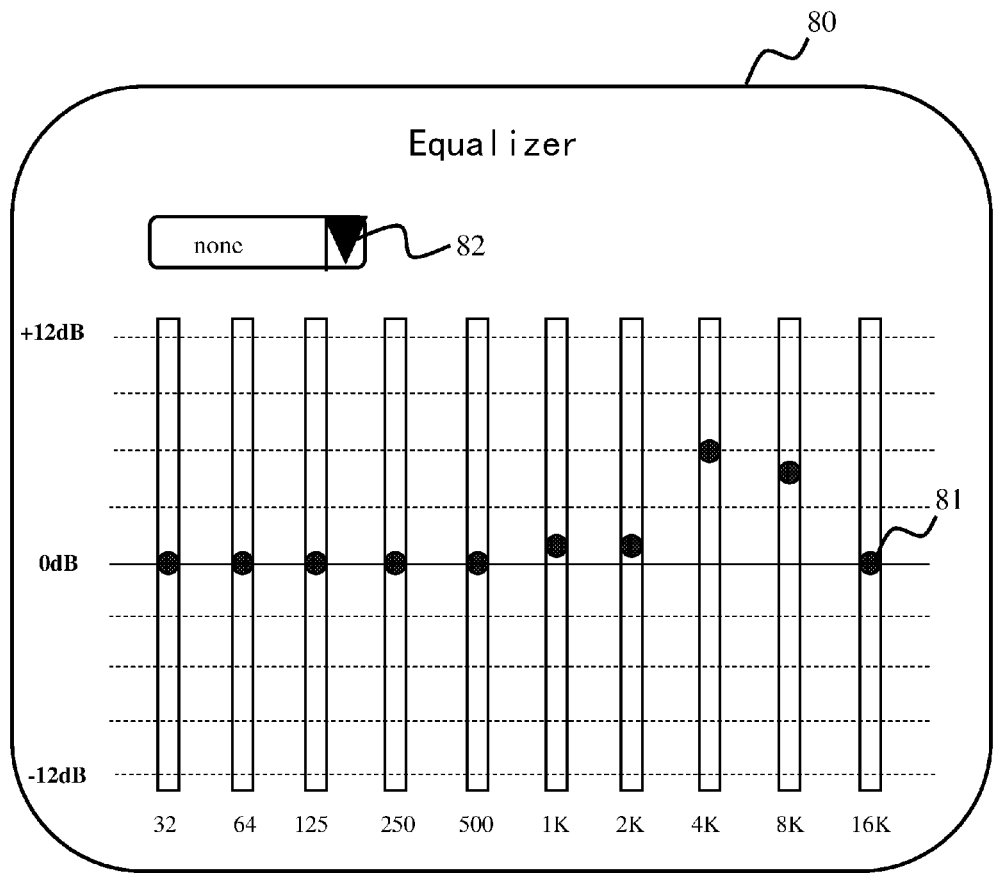
FIG. 7 is a view of the gain value settings of an equalizer after adjustment in normal mode.
Figure 8:
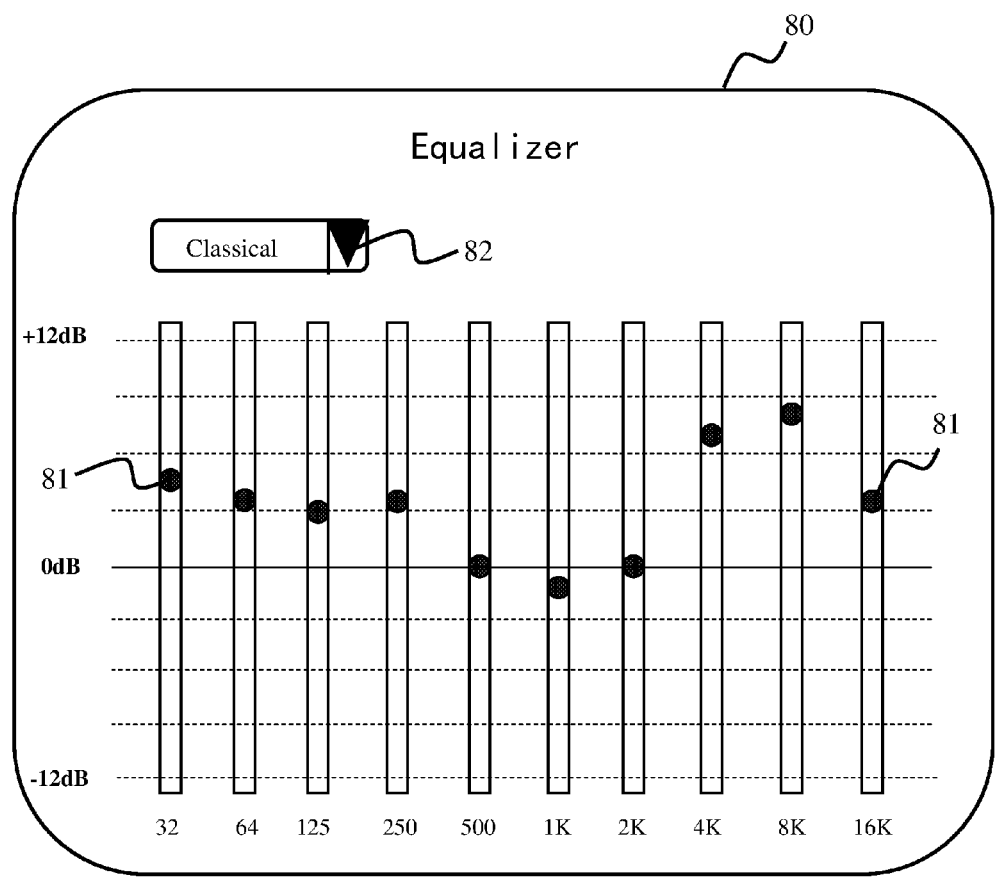
FIG. 8 is a view showing the gain value settings of an equalizer after adjustment in another mode.

After the parameter setting module 30 completes the adjustment operation, the gain values of the equalizer EQ in each mode will be synchronously set to new gain values. Referring again to the above example, the gain value of sounds at the frequency of 4,000 Hz is increased by 6 dB above the original gain value in each mode (as shown in FIGS. 6 and 7), and the settings of other gain values at different frequencies will also be adjusted.

Figure 2:
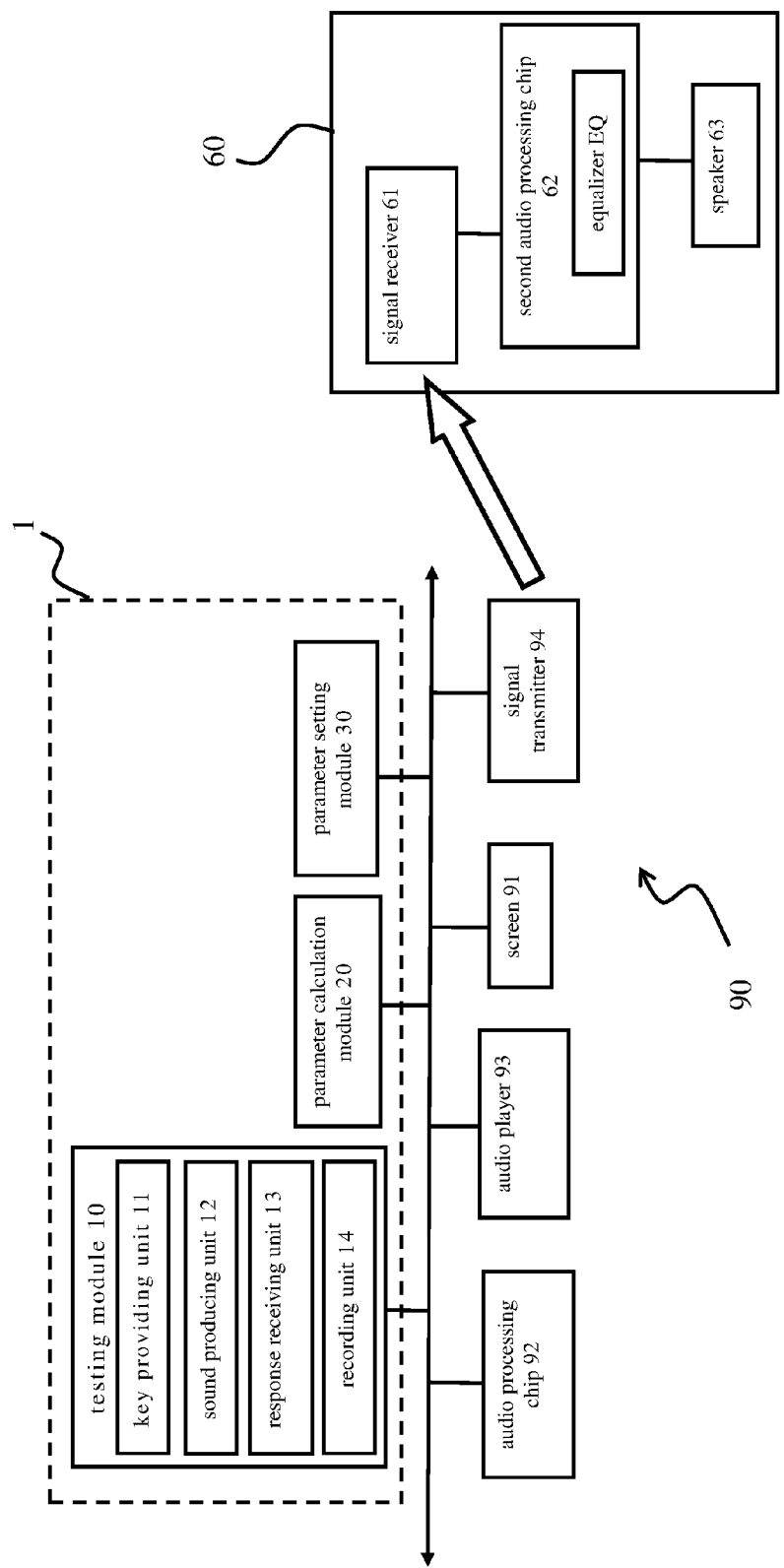
FIG. 2 presents schematically the environment of an electronic device including an equalizer adjustment system according to a second embodiment of the present invention.

FIG. 2 presents a schematic of the environment of an electronic device 90 according to a second embodiment of the present invention. The second embodiment of the present invention differs from the aforementioned first embodiment in that the electronic device 90 further includes an audio playback device 60 and a signal transmitter 94. Specifically, the audio playback device 60 includes a signal receiver 61, a second audio processing chip 62 and a speaker 63. The signal transmitter 94 and the signal receiver 61 are connected with each other by wireless communication technology. In a specific embodiment of the present invention, the audio playback device 60 is a wireless headphone, but the present invention is not limited thereto.

The signal receiver 61 is used to connect with the signal transmitter 94 to receive a parameter setting command generated from the equalizer adjustment system 1 and to receive audio signals (e.g., music) as well. In a specific embodiment of the present invention, both the signal receiver 61 and the signal transmitter 94 are Bluetooth wireless communication modules. In other words, the audio playback device 60 in this embodiment is wirelessly connected with the electronic device 90, but the present invention is not limited thereto.

The second audio processing chip 62 is electrically connected to the signal receiver 61 and the speaker 63 and includes an equalizer EQ. The parameter setting command from the electronic device 90 can be used for adjusting the settings of gain values of sounds at different frequencies of the equalizer, such that the second audio processing chip 62 can process the input sound signals according to the settings of the adjusted gain values of the equalizer EQ to generate an output sound signal so that the speaker 63 can produce sounds according to the output sound signal. In a specific embodiment of the present invention, the second audio processing chip 6 is a microcontroller, and the equalizer EQ exists in the microcontroller in the form of software (firmware), but the present invention is not limited thereto.

In the second embodiment, the remaining devices or elements with regard to the equalizer adjustment system and the electronic device 90 which are not covered have functions similar to those of the aforementioned first embodiment, so the details of those functions will not be repeated herein.

As described above, the equalizer adjustment system 1 of the present invention can provide a hearing test procedure. After a user completes a hearing test, the equalizer adjustment system 1 can adjust the setting of the equalizer EQ according to the results of the hearing test such that sound issued by the electronic device 90 or the audio playback device 60 can be adjusted to compensate for the user's condition of hearing.

Figure 9:
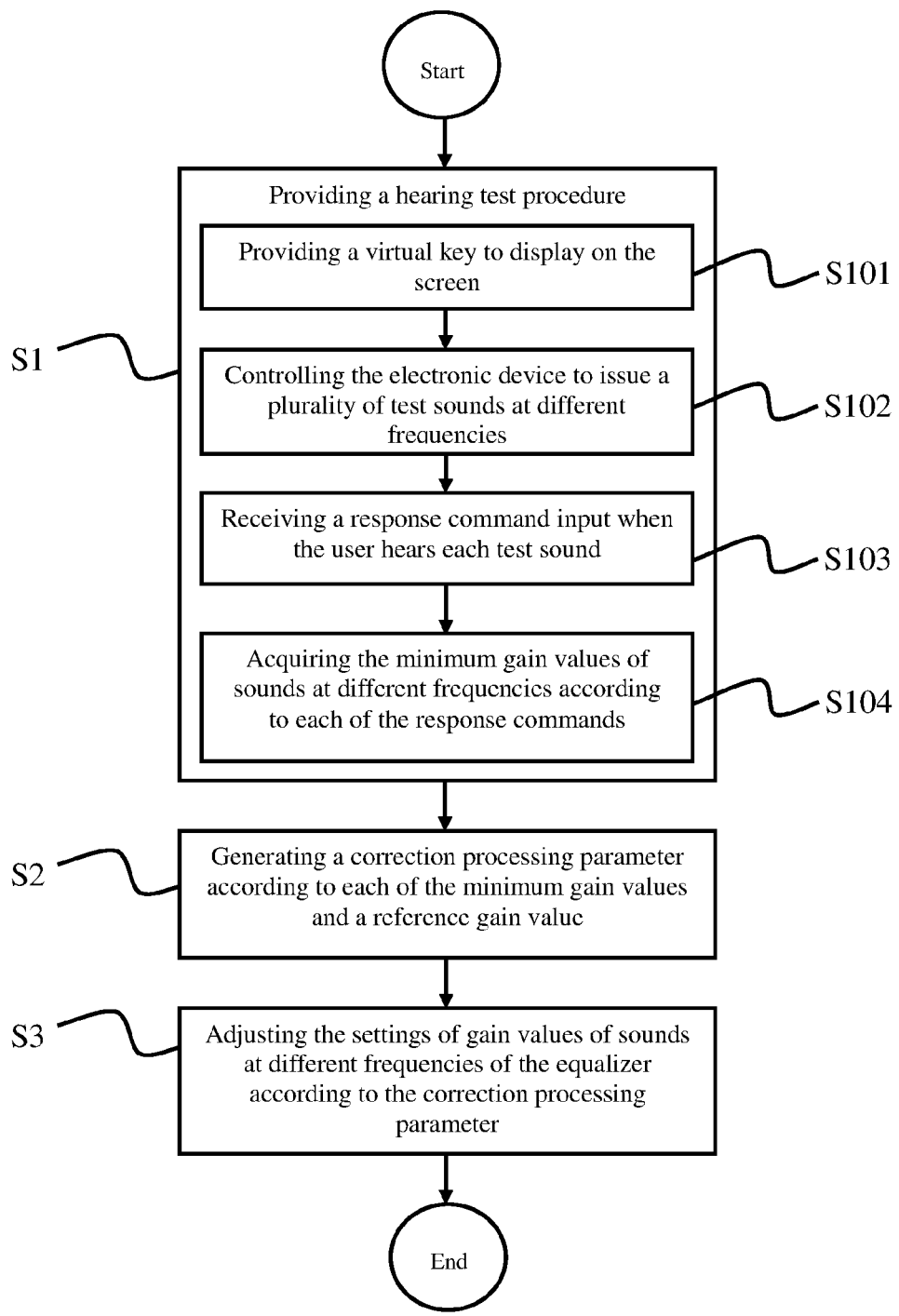
FIG. 9 is a flowchart showing a method of adjusting an equalizer according to the present invention.

Finally, please refer to all of FIGS. 1-9, in which FIG. 9 is a flowchart showing a method of adjusting an equalizer. Hereinafter, each of the steps presented in FIG. 9 will be described in sequence in conjunction with FIGS. 1-8. It should be noted that although the following description uses the electronic device 90 shown in FIG. 1 or FIG. 2 as an example to illustrate the equalizer adjustment method disclosed in the present invention, the present invention is not limited to using the aforementioned electronic device 90 to implement the equalizer adjustment method.

First, in Step S1: Providing a hearing test procedure.

In the equalizer adjustment method disclosed in the present invention, the gain value setting of the equalizer EQ can be adjusted according to the user's physiological condition of hearing. Therefore, to determine the user's physiological condition of hearing, the first step of the equalizer adjustment method is to provide a hearing test procedure. After the user completes the hearing test procedure, the minimum gain values at which sounds at different frequencies can be heard by the user are acquired.

In an embodiment of the present invention, in Step S1, the step of providing a hearing test procedure includes steps S101, S102, S103, and S104.

In Step S101: Providing a virtual key to display on the screen.

Once the hearing test procedure is started, the key providing unit 11 of the testing module 10 will provide the virtual key 71 as shown in FIG. 5 for display on the screen 91.

In Step S102: Controlling the electronic device to issue a plurality of test sounds at different frequencies.

After providing the virtual key 71, the sound producing unit 12 of the testing module 10 will then control the audio player 92 or the audio playback device 60 (in the aforementioned second embodiment) of the electronic device 90 to issue a plurality of test sounds at different frequencies In Step S103: Receiving a response command input when the user hears each test sound.

Once the user hears the test sound, the user can press the virtual key 71 to input a response command which will be received by the response command unit 13 of the testing module 10.

In Step S104: Acquiring the minimum gain values of sounds at different frequencies according to each of the response commands.

After acquiring different frequencies, the user can hear the sound with the minimum gain value. Then the recording unit 14 of the testing module 10 can acquire and record each minimum gain value at which sounds at different frequencies can be heard by the user according to each of the response commands.

The completion of the hearing test procedure is followed by Step S2: Generating a correction processing parameter according to each of the minimum gain values and a reference gain value.

After the minimum gain values at which sounds at different frequencies can be heard by the user are acquired through the implementation of the hearing test procedure, the parameter calculation module 20 can generate a correction processing parameter according to each of the minimum gain values and a reference gain value acquired from the test. In an embodiment of the present invention, the parameter calculation module 20 uses the smallest gain value among the minimum gain values acquired by the test as the reference gain value; in FIG. 6, for example, among a plurality of minimum gain values, the smallest are 10 dB (those at 250 Hz and 500 Hz). Thus, the parameter calculation module 20 will use 10 dB as the reference gain value. In other words, in the present embodiment, the reference gain value is dynamic and can be determined depending on the test results, but the determination of the reference gain value in the present invention is not limited thereto. The reference gain value can also be uniformly preset as a specific gain value (e.g., 20 dB).

In the present embodiment, the parameter calculation module 20 generates correction parameters according to the difference between each of the minimum gain values and the reference gain value. Using 4,000 Hz as an example, if the acquired minimum gain value is 70 dB, the parameter calculation module 20 will generate correction parameters according to the difference of 60 dB between the acquired minimum gain value and the reference gain value. Similarly, the correction parameters at other frequencies are also acquired in this way. Ultimately, the correction parameter set at different frequencies is the correction processing parameter as described above.

Finally, in Step S3: Adjusting the settings of gain values of sounds at different frequencies of the equalizer according to the correction processing parameter.

After the correction processing parameter is generated, the parameter setting module 30 can generate a parameter setting command according to the correction processing parameter. The parameter setting command can adjust the settings of gain values of sounds at different frequencies of the equalizer EQ so that the sound output by the electronic device 90 is modified to compensate for the test participant's condition of hearing, and the sound output can achieve the best results for the user.

As described above, the objective, means, and efficiency of the present invention are all different from conventional characteristics in the prior art. However, it should be noted that the described embodiments are only for illustrative and exemplary purposes, and that various changes and modifications may be made to the described embodiments without departing from the scope of the invention as disposed by the appended claims.

What is claimed is:

1. An electronic device, comprising:
   an equalizer; and
   an equalizer adjustment system, which is used for adjusting the settings of the equalizer, the equalizer adjustment system comprising:
   a testing module, which is used for providing a hearing test procedure so as to acquire a plurality of minimum gain values at which sounds at different frequencies can be heard by a user after the user finishes the hearing test procedure;
   a parameter calculation module, which is used for generating a correction processing parameter according to each of the minimum gain values and a reference gain value; and
   a parameter setting module, which is used for adjusting the settings of gain values of sounds at different frequencies of the equalizer according to the correction processing parameter,
   wherein the reference gain value is (10×N) dB, (0<N<20), and N is an integer, and
   wherein when each of the minimum gain values is greater than the reference gain value, the parameter setting module increases by N the gain values of sounds corresponding to each of the frequencies of the equalizer.

2. The electronic device as claimed in claim 1, further comprising an audio processing chip.

3. The electronic device as claimed in claim 2, wherein the equalizer is disposed in the audio processing chip.

4. The electronic device as claimed in claim 1, further comprising an audio playback device, which comprises a second audio processing chip and a speaker.

5. The electronic device as claimed in claim 4, wherein the equalizer is disposed in the audio playback device.

6. The electronic device as claimed in claim 5, wherein the equalizer is disposed in the second audio processing chip.

7. The electronic device as claimed in claim 6, wherein the reference gain value is the smallest of the minimum gain values.

8. The electronic device as claimed in claim 6, wherein when each of the minimum gain values is greater than the reference gain value 10×N dB, the parameter setting module increases the gain values of sounds corresponding to each of the frequencies of the equalizer N dB, wherein 0<N<20, and N is usually an integer when doing a test.

9. The electronic device as claimed in claim 6, wherein the testing module further comprises:
   a sound producing unit, which is used for making a plurality of test sounds with different frequencies;
   a response receiving unit, which is used for receiving a response command inputted by a user when the user hears each of the test sounds; and
   a recording unit, which is used for acquiring each of the minimum gain values at which the sounds at different frequencies can be heard by the user according to each of the response commands.

10. The electronic device as claimed in claim 9, wherein the electronic device further comprises a screen and the testing module further comprises a key providing unit, which is used for displaying a virtual key on the screen so that the user can select and input each of the response commands.

11. The electronic device as claimed in claim 1, wherein the reference gain value is the smallest of the minimum gain values.

12. The electronic device as claimed in claim 1, wherein the testing module further comprises:
   a sound producing unit, which is used for making a plurality of test sounds with different frequencies;
   a response receiving unit, which is used for receiving a response command inputted by a user when the user hears each of the test sounds; and
   a recording unit, which is used for acquiring each of the minimum gain values at which sounds at different frequencies can be heard by the user according to each of the response commands.

13. An audio playback device, which is electrically connected to an electronic device having a first audio processing chip,
   the electronic device comprising:
   a testing module, which is used for providing a hearing test procedure so as to acquire a plurality of minimum gain values at which sounds at different frequencies can be heard by a user after the user finishes the hearing test procedure;
   a parameter calculation module, which is used for generating a correction processing parameter according to each of the minimum gain values and a reference gain value; and
   a parameter setting module, which is used for adjusting the settings of gain values of sounds at different frequencies of the equalizer according to the correction processing parameter, and the audio playback device comprising:

a second audio processing chip;

a signal receiver, which is electrically connected to the second audio processing chip for receiving a parameter setting command from the electronic device; and an equalizer, in which the parameter setting command is used for adjusting the settings of gain values of sounds at different frequencies, wherein the reference gain value is (10×N) dB, (0<N<20), and N is an integer, and wherein when each of the minimum gain values is greater than the reference gain value, the parameter setting module increases by N the gain values of sounds corresponding to each of the frequencies of the equalizer.

14. The audio playback device as claimed in claim 13, wherein the equalizer is disposed in the second audio processing chip.

15. A method for adjusting an equalizer, which is applied to an electronic device and used to adjust the settings of an equalizer, the method for adjusting the equalizer comprising the following steps:

providing a hearing test procedure so as to acquire a plurality of minimum gain values at which sounds at different frequencies can be heard by a user after the user finishes the hearing test procedure;

generating a correction processing parameter according to each of minimum gain values and a reference gain value; and adjusting the settings of gain values of sounds at different frequencies of the equalizer according to the correction processing parameter, wherein the reference gain value is (10×N) dB, (0<N<20), and N is an integer, and wherein when each of the minimum gain values is greater than the reference gain value, the gain values of sounds corresponding to each of the frequencies of the equalizer are increased by N.

16. The method for adjusting an equalizer as claimed in claim 15, wherein the reference gain value is the smallest of the minimum gain values.

17. The method for adjusting an equalizer as claimed in claim 15, wherein providing the hearing test procedure comprises the steps of:

controlling the electronic device to make a plurality of test sounds at different frequencies;

receiving a response command inputted by a user when the user hears each of the test sounds; and acquiring each of the minimum gain values at which the sounds at different frequencies can be heard by the user according to each of the response commands.

18. The method for adjusting an equalizer as claimed in claim 17, wherein the electronic device comprises a screen, the step of providing the hearing test procedure further comprising the following step:

providing a virtual key to display on the screen so that the user can select and input each of the response commands.

* * * * *